United States Patent
Sykes

(10) Patent No.: US 6,178,823 B1
(45) Date of Patent: Jan. 30, 2001

(54) APPARATUS AND METHOD FOR TESTING BOND STRENGTH OF ELECTRICAL CONNECTION

(75) Inventor: Robert Sykes, Tendring (GB)

(73) Assignee: Dage Precision Industries, Ltd. (GB)

( * ) Notice: Under 35 U.S.C. 154(b), the term of this patent shall be extended for 0 days.

(21) Appl. No.: 09/322,331

(22) Filed: May 28, 1999

(30) Foreign Application Priority Data

Jun. 3, 1998 (GB) .................................... 9811795

(51) Int. Cl.$^7$ ...................................... G01N 3/08
(52) U.S. Cl. ............................... 73/827; 73/150 A
(58) Field of Search ............................ 73/826, 827, 828, 73/150 A

(56) References Cited

U.S. PATENT DOCUMENTS

| | | | | |
|---|---|---|---|---|
| 4,055,992 | * | 11/1977 | Pizzarello | 73/791 |
| 4,453,414 | * | 6/1984 | Ronemus et al. | 73/827 |
| 4,895,028 | * | 1/1990 | Mayer | 73/827 |
| 5,275,058 | * | 1/1994 | Pham et al. | 73/827 |
| 5,894,981 | * | 4/1999 | Kelly | 228/104 |

* cited by examiner

*Primary Examiner*—Max Noori
(74) *Attorney, Agent, or Firm*—Kilpatrick Stockton

(57) ABSTRACT

An apparatus and method for testing angled strand connections in a miniature electrical device includes a test tool movable simultaneously along two mutually perpendicular axes and perpendicular to the strand direction. The tool measures breaking force along one axis only, the breaking force in the direction of tool movement being calculated by reference to the angle of tool movement. The method gives rapid testing of successive strands with good operator view.

10 Claims, 1 Drawing Sheet

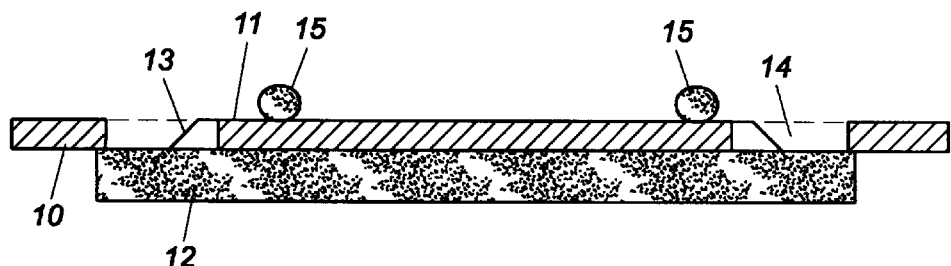
Fig. 1
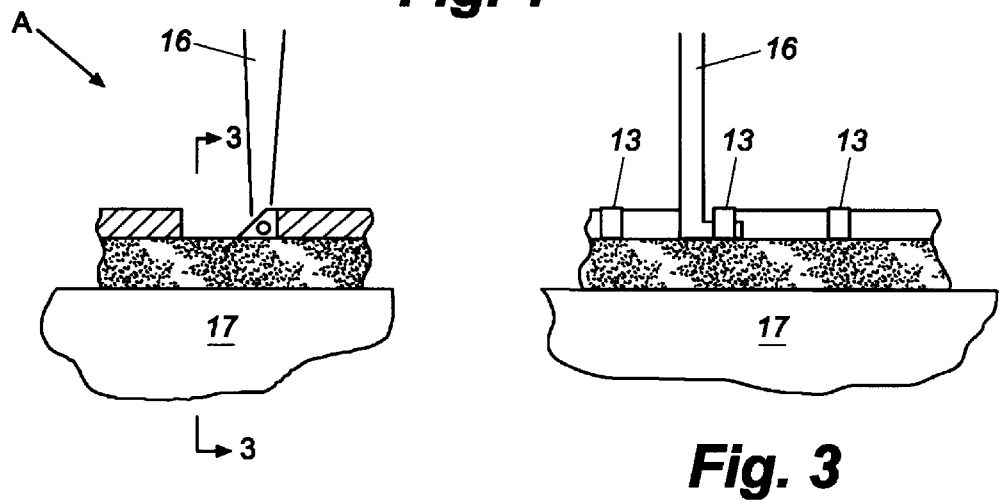
Fig. 2  Fig. 3
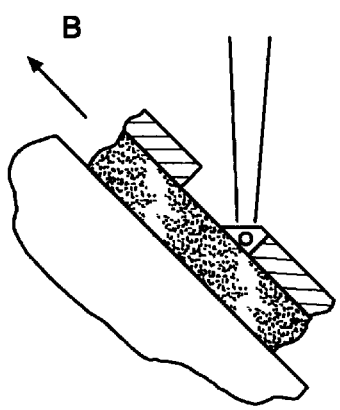
Fig. 4
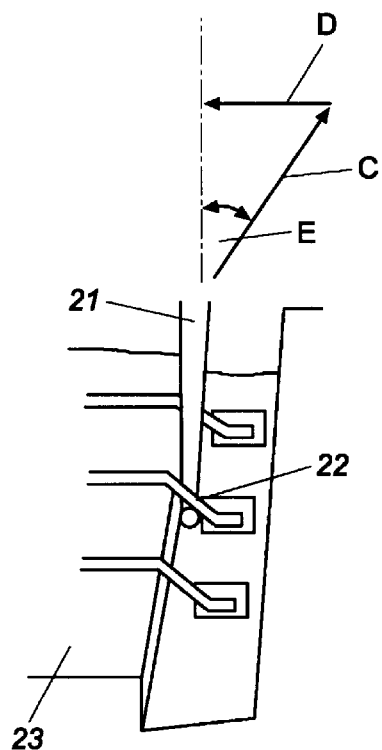
Fig. 5

APPARATUS AND METHOD FOR TESTING BOND STRENGTH OF ELECTRICAL CONNECTION

This invention relates to an apparatus and method for testing the mechanical integrity of connections in miniature electrical circuits.

The physical size of electronic devices, particularly microprocessors, is rapidly reducing, and as a consequence the size of electrical connections must also reduce. A current microprocessor may have an array of edge connections comprising copper strands having a width of 40 μm and a spacing of 250 μm. These edge connections may typically extend around all sides of a rectangular circuit component and are in use bonded to other parts of the device, for example by ultrasonic or thermocompression techniques.

In mass production it is necessary to periodically test the mechanical strength of these bonds, both to ensure that the connection method remains adequate and to give assurance that the electronic device will be reliable in service.

A tensile test can be performed by restraining the device on a horizontal workholder, and hooking the connection strand with a tool. Gripping the strand with mechanical tweezers is also known. A shear test can be performed by pushing the bond site sideways with a tool. In each case the breaking force is measured using appropriate strain gauge methods.

Owing to the very small size of the connection strands it is essential to view the workpart through a magnifying device. The tool is typically mounted on a 3 axis motor drive. Great care is required to minimise friction forces which would otherwise mask the very low breaking forces measured. Precision is a prerequisite since the tool must be guided into engagement with a strand, and perform the test without damaging adjacent strand connections. Speed is also important since the number of connections to be tested is rather high, and thus the test duration has a significant effect on testing costs.

A problem arises in the case of connections which incline relative to the plane of the electrical circuitry. This occurs in the case of printed circuits formed on an insulating substrate, and having connection strands pushed through apertures in the substrate for connection to an electrical device. Typically such strands may lie at about 45°.

In a tensile test a hook tool tends to slip up the strand to a greater or lesser extent, and in a manner which is neither consistent nor repeatable. The position of the hook on the strand is however important since the proportion of tensile load taken at opposite ends of the strand will change if the hook position moves. This effect is especially noticeable in short strands of the kind found in miniature devices. The variation in measured force due to slipping of the hook is more than sufficient to mask the test result.

One solution to this problem is to place the device at an angle so that the connection strand is generally perpendicular to the direction of pull. This can give a consistent result because the tool is not prone to slipping, but placing the device at an angle brings other problems. Firstly if the device is wide, it may interfere with free movement of the test head. Secondly, operator view of the device may be poor, and thus positioning of the tool imprecise. Thirdly movement of the device between adjacent rows of strands requires unclamping, indexing, reclamping and refocusing of the magnifying device; this has significant manipulation difficulties, and is time consuming.

Another solution provides a stiffer hook tool with support bearings adjacent the tip thereof. However the inherent tool stiffness cannot be greatly increased without increasing the section thereof, and thus risking contact damage to the device during tool manipulation. Furthermore, the additional bearings introduce an additional source of friction, restrict the range of free movement of the test head, and may also restrict operator visibility. A better solution is required.

According to the invention there is provided an apparatus for testing the bond strength of strand connections in a miniature electrical component, the apparatus including a workholder, a test head movable over the workholder and having a 2-axis drive, one drive axis being operable simultaneously with the other drive axis, a test tool on the test head, a strain gauge adapted to measure force at the tool along one of said axes, and control means adapted to drive the test head at an acute angle to one of said axes.

Preferably the workholder is movable in a plane perpendicular to one of said axes, in translation and/or rotation. In the preferred embodiment the workholder is horizontal. A 3-axis drive is preferably provided for optimum tool manipulation; this provides greater freedom in choosing the direction of pull, and consequently greater freedom of workpart placement and the likelihood of optimum operator visibility.

According to a further aspect, the invention provides a method of testing the bond strength of strand connections in a miniature electrical component, and in which the strand direction lies at an angle to the plane of the component substrate, the method comprising the steps of:

orientating said substrate in a first plane perpendicular to a first axis;

hooking said strand with a test tool;

moving said test tool perpendicular to the direction of said strand, by simultaneous movement of said test tool along a first axis and a second mutually perpendicular axis;

calculating the angle of movement of said test tool with respect to the plane of said substrate;

measuring the breaking force of said strand along one of said first and second axes; and calculating by reference to said angle the breaking force of said strand in the direction of movement of said test tool.

This test apparatus and method is both elegant and counterintuitive. Conventionally the skilled man would look for a solution to the existing problem by providing an improved test head better able to resist lateral forces, or an improved workholder, or more rapid refocusing techniques, or some other improvement directly addressing one of the prior test difficulties. The present invention relies on the realisation that a computerised 2-axis motor drive for this kind of test apparatus must inherently be very precise since accurate positioning of the test tool is necessary. Simultaneous operation of the drive motors along two or three axes does not affect the workholder or the test head. Furthermore the breaking loads to be measured are very small, and thus no special upgrading or adaptation of the drive motor perpendicular to the normal test axis is required; in other words the positioning drive motor has sufficient capacity to exert the necessary test force, without adaptation.

Finally, the use of geometrical techniques to calculate the actual breaking force means that a known low friction test head can be used, and this avoids the problem of introducing additional frictional forces by adaptation of the mechanism to overcome problems in a conventional manner.

The invention has the particular advantage that the test machine can be used both for vectored tests according to the invention, and unidirectional tests without significant adaptation. Importantly, the device is mounted on a generally horizontal workholder, and thus facilitates indexing and rotation without requiring refocusing of the magnifying device. In particular the device can easily be oriented to give the operator a good view of the array of angled connection strands, without refocusing.

Another advantage of the invention is that the test head can be driven at any desired angle and velocity by adjusting the relative speeds of the drive motors. In this way a truly perpendicular pull is assured, and a fixed angle is not required for a particular array of strands. Thus the most appropriate manufacturing method can be adopted, and the direction of pull selected to suit the actual angle of the strands. Variation of the strand angle is easily accommodated by reprogramming of the drive motors, and no adjustment of the workholder is required. In particular, specialised jigs to hold different electrical devices at suitable angles are not required, and thus there is no consequent loss of time when a different device is to be tested. Furthermore there is no need to take special steps where collision between an angled device and the test head may occur.

Other features of the invention will be apparent from the following description of a preferred embodiment shown by way of example only in the accompanying drawings in which:

FIG. 1 is a transverse section through miniature electrical device.

FIG. 2 corresponds to FIG. 1 and illustrates a prior method of testing bond strength.

FIG. 3 is a longitudinal section on line 3—3 of FIG. 2.

FIG. 4 illustrates an alternative prior test method.

FIG. 5 is an isometric view illustrating the present invention.

FIG. 1 illustrates a transverse cross-section through a typical miniature printed circuit having angled connection strands.

An insulating substrate 10, of e.g. Mylar, has deposited thereon a film of copper 11. The copper film (indicated by the thick line) is masked to define the required electrical tracks, and the exposed copper dissolved, followed by the masking. This leaves the required copper tracks deposited on the substrate 10, and is a conventional manufacturing method.

The substrate is placed over an electrical device (or die) 12 and the copper strands 13 are pushed from the position indicated in dotted line in FIG. 1 through apertures 14 in the substrate to be bonded by thernocompression techniques to connection sites on the device 12. The drawing has somewhat exaggerated dimensions in order to illustrate the construction more clearly. The connection strands 13 are at about 45°.

The apertures 14 in the substrate may be formed in any suitable manner, either before or after the copper tracks are formed; solder balls 15 permit connection from the electrical tracks to other componentry.

The embodiment illustrated has a plurality of connection strands on either side of the component and extending in two rows perpendicular to the plane of the drawing.

FIGS. 2 and 3 illustrates a first prior test technique in which the component is clamped to a workholder 17, and a test tool 16 is hooked under a connection strand. The tool is driven vertically upward to measure the breaking force of the strand using suitable strain gauge techniques. In use, the tool 16 tends to slide up the strand 13, thus giving a varying proportion of force between the two ends thereof; this is sufficient to mask the true breaking force. Furthermore the tool 16 may bend since the section thereof is small. Yet another problem is that a test apparatus designed to measure tensile forces, and particularly the strain gauge arrangement, may not be able to resist the lateral forces inevitable in this technique.

FIG. 3 illustrates the typical row of connection strands 13, which must be tested sequentially. Provided that precise positioning and clamping arrangements are provided, the workholder can be indexed laterally with respect to the operator, thus maintaining the bond sites in focus of the necessary magnifying device. It is preferably for the operator to view from the direction indicated by arrow A in order to have sight of the bond site for accurate tool manipulation. A second row of bond sites can be tested by shifting the workholder in the horizontal plane (either laterally or pivotally) until the row is perpendicular to the line of sight. No adjustment of the magnifying device is required provided that accurate control of the position of the workholder can be assured.

FIG. 4 illustrates an alternative prior technique in which the component is mounted at an angle relative to the application of force. In this case a purely tensile load can be applied since the strand 13 is perpendicular to the direction of pull. There are however a number of disadvantages with this technique. If the component is wide (in the direction of arrow B) it may interfere with free movement of the test mechanism. The line of sight of the operator may be obscured. The most serious disadvantage is however that testing of a second row of bond sites requires unclamping of the component, indexing of the workholder, reclamping of the component and refocusing of the magnifying device. This is very time consuming and increases the test time substantially. Furthermore there is a danger that the component, which is usually very small, may drop off the workholder during repositioning.

FIG. 5 illustrates the solution to the problems of the prior art testing methods. In essence the drive motors of 2-axis are utilised to apply an angled pull to the connection strand, typically by operating X and Z axis motors at the same time. The test head need be calibrated to measure breaking force in one direction only; the actual breaking force being calculated by routine geometrical techniques.

As illustrated, the test tool 21 is engaged under a strand connection 22 of a device 23 which is mounted in a generally horizontal plane, and oriented for good operator view. The tool is driven simultaneously upward and to the side, as represented by arrow C to give a pull substantially perpendicular to the general direction of the strand. In the preferred example, the test tool is mounted to a conventional shear test head, and is thus capable of resisting significant side loads. The shear test head will measure a horizontal component D of the force, and in particular the breaking load. The actual breaking load perpendicular to the strand can be calculated from a knowledge of the angle E at which the test head moves; this angle can be calculated from the relative displacement along the X and Y axes from the datum position. If necessary the angle E can be readily adjusted by reprogramming of the drive motors, and the apparatus is thus readily adaptable to devices having a different strand angle, or to devices in which the strand angle may have changed due to a variation of production method. The desired pull angle may be input by an operator, and effected by appropriate displacement along the X and Y axes.

In use the perpendicular pull ensures that there is no possibility of the test tool slipping along the strand, and thus the test method is both repeatable and reliable.

In a final step, the test head may bend a broken strand back on itself so as not to interfere with free movement of the test head or obscure view.

Various embodiments of the invention are possible within the scope of the claims appended hereto.

What is claimed is:

1. Apparatus for testing the bond strength of strand connections in a miniature electrical component, the apparatus including a workholder and comprising:
   a test head movable over the workholder and having a 2-axis drive, the drive axes being mutually perpendicular and operable simultaneously and independently;
   a test tool on the test head;
   a strain gauge adapted to measure force at the tool along one of said axes; and
   control means adapted to drive the test head simultaneously and independently in the plane of said axes and at a predetermined acute angle to one of said axes, so that the test tool moves substantially perpendicular to a strand connection engaged by the test tool.

2. Apparatus according to claim 1 wherein the workholder is movable in a plane perpendicular to one of said axes, in translation.

3. Apparatus according to claim 1 wherein the workholder is movable in a plane perpendicular to one of said axes, in rotation.

4. Apparatus according to claim 1 wherein the workholder is in a horizontal plane.

5. Apparatus according to claim 1 wherein said test head has a 3-axis drive.

6. A method of testing the bond strength of strand connections in a miniature electrical component, and in which the strand direction lies at an angle to the plane of the component substrate, the method comprising the steps of:
   orientating said substrate in a first plane perpendicular to a first axis;
   hooking said strand with a test tool;
   moving said test tool perpendicular to the direction of said strand, by simultaneous movement of said test tool along a first axis and a second mutually perpendicular axis;
   calculating the angle of movement of said test tool with respect to the plane of said substrate;
   measuring the breaking force of said strand along one of said first and second axes; and
   calculating by reference to said angle the breaking force of said strand in the direction of movement of said test tool.

7. A method of testing according to claim 6 and including the additional step of hooking said strand by movement of said test tool along a third mutually perpendicular axis.

8. A method of testing according to claim 6 and including the final step of using said test tool to bend the broken strand against said substrate.

9. A method of testing according to claim 7 and including the final step of using said test tool to bend the broken strand against said substrate.

10. A method according to claim 6, and including the preparatory steps of:
   securing said substrate on a rotatable workholder; and
   rotating said workholder so that said strand is in the plane of said first and second axes.

* * * * *